US006624312B2

(12) United States Patent
Mann

(10) Patent No.: US 6,624,312 B2
(45) Date of Patent: Sep. 23, 2003

(54) REVERSE CRYSTALLIZATION AND PURIFICATION OF NITROGEN CONTAINING FLAVOR AND FRAGRANCE CHEMICALS AND METHODS RELATED THERETO

(76) Inventor: Morris Mann, 21669 N. 57th Ave., Glendale, AZ (US) 85308

( * ) Notice: Subject to any disclaimer, the term of this patent is extended or adjusted under 35 U.S.C. 154(b) by 0 days.

(21) Appl. No.: 09/793,472

(22) Filed: Feb. 26, 2001

(65) Prior Publication Data

US 2002/0127179 A1 Sep. 12, 2002

Related U.S. Application Data

(60) Provisional application No. 60/187,677, filed on Mar. 8, 2000.

(51) Int. Cl.$^7$ .................... C07D 261/20; C07D 209/04; C07C 211/02

(52) U.S. Cl. ........................ 548/241; 548/469; 564/305

(58) Field of Search ................................ 548/241, 469; 564/305

(56) References Cited

PUBLICATIONS

Slizhov, et al, 1979, Koks i Khimiya, 12, 27–8.*

* cited by examiner

*Primary Examiner*—Joseph K. McKane
*Assistant Examiner*—Andrea D. Small
(74) *Attorney, Agent, or Firm*—The Halvorson Law Firm

(57) ABSTRACT

A method for purifying various nitrogen containing flavor and fragrance compounds is described. The method comprises at least one step of reverse crystallization for liquid compounds and may be followed by at least one step of forward crystallization for compounds that are solid at room temperature.

10 Claims, 2 Drawing Sheets

REVERSE CRYSTALLIZATION AND PURIFICATION OF NITROGEN CONTAINING FLAVOR AND FRAGRANCE CHEMICALS AND METHODS RELATED THERETO

CROSS-REFERENCE To RELATED APPLICATIONS

This applicant claims the benefit of U.S. Provisional Application No. 60/187,677, filed Mar. 8, 2000.

FIELD OF THE INVENTION

The present invention is generally directed towards purification techniques involving flavors and fragrance chemicals. More specifically, the present invention is directed to a method for the removal of impurities in synthetic nitrogen containing flavor and fragrance compounds.

BACKGROUND OF THE INVENTION

The fragrance and flavor industries utilize a wide variety of natural and synthetic compounds in their formulations. The concentration of certain nitrogen containing flavor and fragrance compounds that are used extensively in these respective industries is limited because of the unpleasant odors of the synthetic versions. Traditionally, these unpleasant odors have been considered characteristic. In fact they occur due to the synthesis process. Therefore, there is a need in the art for technology that would allow clean, easy and efficient purification of the nitrogen containing components.

SUMMARY OF THE INVENTION

It is an object of the present invention to provide a method for the purification of nitrogen containing cyclic compounds that uses at least one step of reverse crystallization to remove unwanted impurities.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DESCRIPTION OF THE PREFERRED EMBODIMENTS

Figure 1:
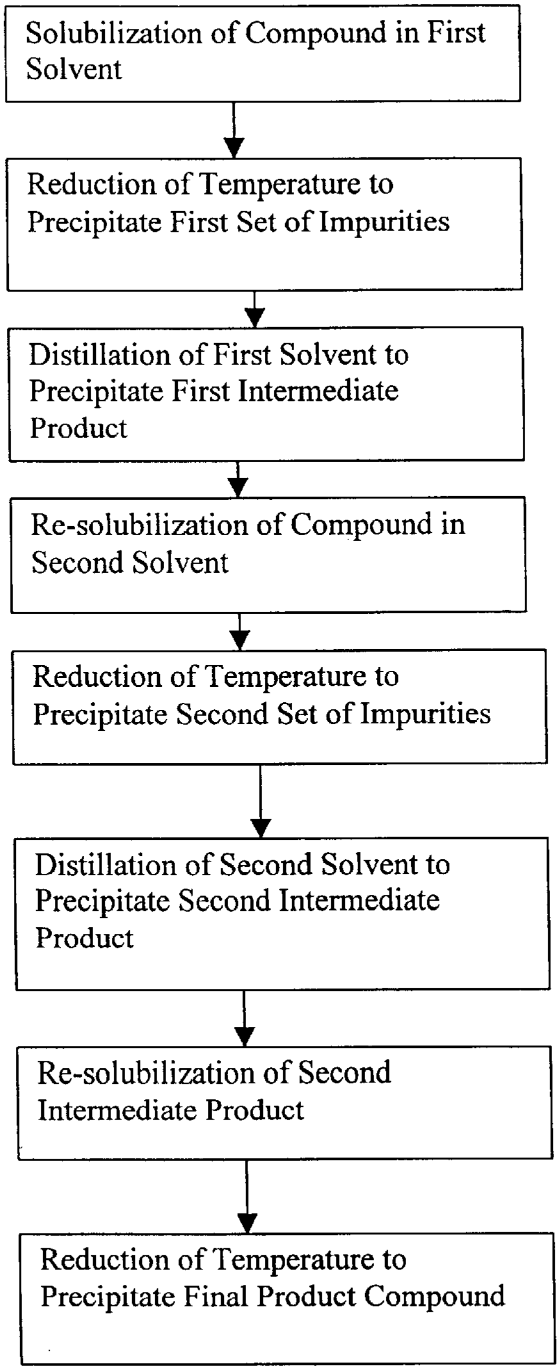
FIG. 1 is a flow diagram of the method according to the present invention used on a solid phase final product
Figure 2:
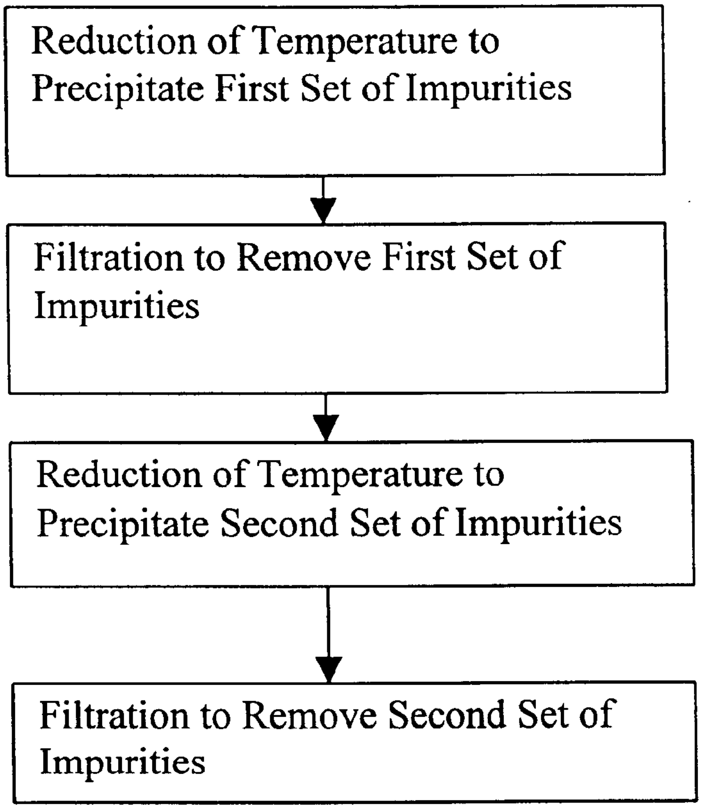
FIG. 2 is a flow diagram of the method according to the present invention used on a liquid phase final product.

The present invention is a method for the purification of a certain class of nitrogen containing compounds frequently used in the fragrance and flavor industry.

The compounds that are the subject to the method according to the present invention are all cyclic systems that contain nitrogen. They include, but are not limited to indole, skatole, various anthranilates, and other like nitrogen bearing cyclic compounds. Synthetic flavor and fragrance molecules containing an nitrogen and a ring structure, such as indole, skatole, and the like, very often have an unpleasant odor not necessarily in keeping with their odor in nature. As an example, synthetic indole purified by layer chromatography has an odor akin to that of orange blossoms, whereas bulk synthetic indole is known for its fecal odor. This disparity is fragrance is due to an as yet unknown impurity that arises during the synthetic process. The elimination of this impurity can be accomplished through the following technique:

Indole is first solubilized in a solvent such as benzene. The minimum amount of solvent to induce solubilization is used. Half again as much solvent is then added to this mixture.

Dry ice is then used to reduce the temperature of the mixture. This produces a chalky white powder that appears on the surface of the Indole-solvent solution. The chalky white powder is separated from the mother liquor by filtration and discarded as waste material. This is a reverse crystallization step.

The remaining solvent is slowly removed either by thermal distillation or vacuum distillation. Vacuum distillation is the preferable method to remove the solvent since the yield is higher. The slow distillation of the solvent produces crystals. This is a forward crystallization step.

The crystals produced in the distillation process are then solubilized in 50% heptane—50% hexane solution. Obviously, other like solvent materials can be used without altering the spirit or character of the invention. The minimum amount of solvent is used while heating and stirring vigorously and/or using ultrasound solubilization to produce a clear supersaturated solution.

The temperature of this supersaturated solution is then reduced with dry ice. Crystals will again form and precipitate. The solvent is removed by filtration or by high vacuum distillation. Once again, vacuum is the preferred embodiment for the purpose of yield. This is a forward crystallization step.

A final optional forward crystallization is may be performed using methanol. Enough methanol is applied to the above crystals to induce solubilization once again using heat and vigorous stirring and/or ultrasound to create a supersaturated solution.

The temperature of this final supersaturated solution is again reduced with dry ice and the resultant final precipitate is dried using filtration and high vacuum. The resultant dry flakes are pure indole and have an odor characteristic of orange blossoms. This surprising result can be easily modified for other nitrogen containing materials, such as skatole and methyl anthranilate.

Compounds such as methyl anthranilate, being liquids at room temperature, responds similarly to solid compounds, such as indole, but without need of any solvent. Chilling the liquid with ice or solid carbon dioxide will induce the appearance of the previously mentioned contaminants, which can be easily removed by high vacuum filtration. This procedure of reverse crystallization can be repeated more than once depending on the degree of purification desired. In any case, one is left with a pure product that can be used at high concentration in flavor or fragrance chemistry.

Clearly, the use of crystallization to induce purification is not novel. However, the use of "reverse" crystallization to remove impurities, the impurities being the resultant crystals, is novel for nitrogen containing flavor and fragrance compounds. This process results in purified chemicals that otherwise would not be available and therefore fulfills a need in the art.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method for the purification of nitrogen containing cyclic systems comprising a) at least one step of reverse crystallization, wherein the step of reverse crystallization is the steps of adding solvent to a compound to solublize the compound and reducing the temperature of the compound to precipitate impurities, and filtrating the precipitate to remove it.

b) at least one step of crystallization to precipitate the compound and where the nitrogen containing cyclic systems are indoles, skatoles, or anthranilates and are foul smelling in their impure state.

2. The method according to claim 1 wherein the step of at least one step of reverse crystallization is two reverse crystallizations.

3. The method according to claim 1 wherein the step of at least one step of crystallization is two crystallizations, both occuring after the step of reverse crystallization.

4. The method according to claim 2 wherein the step of at least one step of crystallization is two forward crystallizations, both occuring after the step of reverse crystallization.

5. The method according to claim 1 wherein the step of reverse crystallization is the steps of adding solvent to a nitrogen containing cyclic compound to solubilize the compound, reducing the temperature of the compound to precipitate impurities, removing the precipitated impurities, and distillation of the remaining solvent to precipitate the compound.

6. The method according to claim 2 wherein the step of reverse crystallization is the steps of adding solvent to a nitrogen containing cyclic compound to solubilize the compound, reducing the temperature of the compound to precipitate impurities, removing the precipitated impurities, and distillation of the remaining solvent to precipitate the compound.

7. The method according to claim 4 wherein the step of reverse crystallization is the steps of adding solvent to a nitrogen containing cyclic compound to solubilize the compound, reducing the temperature of the compound to precipitate impurities, removing the precipitated impurities, and distillation of the remaining solvent to precipitate the compound.

8. The method according to claim 1 the step of crystallization is the steps of adding solvent to a nitrogen containing cyclic compound to solublize the compound and reducing the temperature of the compound to precipitate product compounds.

9. The method according to claim 3 wherein the step of crystallization is the steps of adding solvent to a nitrogen containing cyclic compound to solublize the compound and reducing the temperature of the compound to precipitate product compounds.

10. The method according to claim 4 wherein the step of crystallization is the steps of adding solvent to a nitrogen containing cyclic compound to solublize the compound and reducing the temperature of the compound to precipitate product compounds.

* * * * *